US012714885B2

(12) United States Patent
Kenney et al.

(10) Patent No.: US 12,714,885 B2
(45) Date of Patent: Aug. 25, 2026

(54) SYSTEMS AND METHODS FOR IMMERSION MECHANOTHERAPY

(71) Applicant: Mechanobiologics, Inc., Galveston, TX (US)

(72) Inventors: Linda Jean Kenney, Galveston, TX (US); Michael P. Sheetz, Galveston, TX (US); Felix Margadant, Galveston, TX (US)

(73) Assignee: Mechanobiologics, Inc., Santa Fe, NM (US)

( * ) Notice: Subject to any disclaimer, the term of this patent is extended or adjusted under 35 U.S.C. 154(b) by 635 days.

(21) Appl. No.: 17/515,025

(22) Filed: Oct. 29, 2021

(65) Prior Publication Data

US 2022/0047894 A1 Feb. 17, 2022

Related U.S. Application Data

(63) Continuation-in-part of application No. PCT/US2020/030488, filed on Apr. 29, 2020, and a continuation-in-part of application No. PCT/US2020/030288, filed on Apr. 28, 2020.

(60) Provisional application No. 62/841,520, filed on May 1, 2019, provisional application No. 62/840,850, filed on Apr. 30, 2019.

(51) Int. Cl.

| | |
|---|---|
| ***A61N 7/00*** | (2006.01) |
| ***A61H 33/00*** | (2006.01) |
| ***G16H 20/40*** | (2018.01) |
| ***G16H 30/20*** | (2018.01) |

(52) U.S. Cl.

CPC .......... *A61N 7/00* (2013.01); *A61H 33/6089* (2013.01); *G16H 20/40* (2018.01); *G16H 30/20* (2018.01); *A61N 2007/0004* (2013.01)

(58) Field of Classification Search

CPC .. A61N 2007/0004; A61N 7/00; G16H 20/40; G16H 30/20; A61H 33/6089

See application file for complete search history.

(56) References Cited

U.S. PATENT DOCUMENTS

| | | | |
|---|---|---|---|
| 3,499,437 | A | 3/1970 | Balamuth |
| 4,315,514 | A | 2/1982 | Drewes et al. |
| 6,156,549 | A | 12/2000 | Drewes et al. |
| 6,436,060 | B1 | 8/2002 | Talish |
| 2004/0039416 | A1 | 2/2004 | Myhr |
| 2004/0187876 | A1 | 9/2004 | Myhr |
| 2005/0080341 | A1 | 4/2005 | He et al. |

(Continued)

OTHER PUBLICATIONS

"Tang et al.," "Biological Effects Induced by Non-Thermal Ultrasound and implications for Cancer Therapy, A Review of the Current Literature," Technology in Cancer Research and Treatment vol. 14 No. Apr. 2, 2015 (Year: 2015).*

*Primary Examiner* — Patricia J Park

(74) *Attorney, Agent, or Firm* — Morrison & Foerster LLP

(57) ABSTRACT

Provided is a method for treating metastatic disease or any other tumor that cannot easily or readily localized or localized at all using immersion mechanotherapy. The method includes providing a vessel containing an amount of medium for immersing at least a portion of a subject, and applying one or more programmed cycles of ultrasound waves to the subject through the medium for a pre-determined period of time. Also provided is a device for implementing the immersion mechanotherapy.

38 Claims, 7 Drawing Sheets

(56) References Cited

U.S. PATENT DOCUMENTS

2006/0079816 A1 4/2006 Barthe et al.
2008/0051680 A1 2/2008 Luebcke
2009/0221902 A1 * 9/2009 Myhr ....................... A61N 7/02 601/2
2011/0178441 A1 * 7/2011 Tyler ...................... A61N 5/062 601/2
2014/0107535 A1 * 4/2014 Lin .......................... A61N 1/00 601/2
2017/0107506 A1 * 4/2017 Boer ...................... C12M 41/12
2019/0307427 A1 * 10/2019 Levy ........................ A61B 8/54

* cited by examiner

SYSTEMS AND METHODS FOR IMMERSION MECHANOTHERAPY

CROSS-REFERENCE

This application is a continuation-in-part application claiming priority to co-pending PCT/US2020/030488 filed Apr. 29, 2020, which claims priority to U.S. Provisional Patent Application No. 62/840,850, filed Apr. 30, 2019. This application is a continuation-in-part application claiming priority to co-pending PCT/US2020/030288 filed Apr. 28, 2020, which claims priority to U.S. Provisional Patent Application No. 62/841,520, filed May 1, 2019. All of the previously noted applications are hereby incorporated herein in there entireties, by references thereto, and we claim priority to PCT/US2020/030488 and PCT/US2020/030288 under 35 U.S.C. Sections 120 and 365(c) and to 62/840,850 and 62/841,520 under 35 U.S.C. Section 119.

BACKGROUND

Noninvasive cancer therapy requires high specificity where the treatment selectively targets cancer cells over normal tissues. In particular, it is desired to selectively kill malignant cancer cells over normal somatic cells. In the past, methods have been developed to halt or destroy the tumor by selectively killing cancer cells. For instance, it is known that cell death can be regulated through distinct, and sometimes overlapping, signaling pathways. Manipulation of signaling pathways involved in cell death can be an effective approach in treatment of cancer. In most of those cases, treatments may involve using chemotherapeutic drugs to disrupt signaling pathways that eventually induce cell death. However, this chemo-treatment is often accompanied by serious side effects.

Recently, application of high frequency ultrasound is found to be effective in providing therapeutic heating of tissue, which can be a useful technique in treating diseased tissue such as cancerous tissue. The use of therapeutic heating for treating diseased tissue relies on the effects of hyperthermia on tissue, and those effects can be enhanced by the simultaneous application of radiation, among other ways. Hyperthermia may be achieved by the application of energy in the form of, for example, microwaves, ultrasound waves, or radio-frequency waves. However, such therapy relies on the direct killing of cells by overheating a local treatment zone which may cause discomfort to the user/patient or cause undesired thermal damage to the normal cells.

Moreover, there is no effective treatment for metastatic cancer or metastatic diseases. Metastasis is the spread of cancer cells to new areas of a patient's body, often by way of the lymph system or bloodstream. A metastatic cancer, or metastatic tumor, is one that has spread from the primary site of origin, or where it started, into different areas of the body. Current treatments such as radiation, ablation or therapeutic heating may not be efficient or applicable for metastatic cancer or diseases without exposing a patient to unnecessary medical risks.

SUMMARY

Recognized herein is a need to provide an effective treatment for metastatic cancer or metastatic diseases (e.g., late stage cancer) with improved selectivity as well as reduced side effects. Recognized herein is also a need to provide methods and systems for killing metastasized cells in a non-cytotoxic or comfortable manner.

The present disclosure addresses various aspects of the abovementioned needs by providing an immersion mechanotherapy. In particular, the provided immersion mechanotherapy may manipulate signaling pathways specifically in target cells such as cancer cells or metastasized cells to further treat diseases associated with these signaling pathways in a non-cytotoxic, comfortable and effective manner The immersion mechanotherapy of the present disclosure may provide a novel cancer treatment with high-selectivity or without introducing negative side effects. The treatment may employ methods and systems to trigger the apoptosis induced-cancer cell death utilizing ultrasound waves.

The present disclosure also provides systems and devices for implementing the mechanotherapy in a user-friendly and uniform fashion. The immersion mechanotherapy may be applied to a patient's whole body, a body part or selected portion of the body which is beneficially suitable for treating metastatic diseases. In addition to treating cancer, the provided therapeutic systems or methods may also promote wound healing, tissue repair and tissue regeneration.

The process of recognizing and responding to mechanical stimuli is critical for growth and function of cells. Cells can respond to mechanical signals in the form of forces applied externally or generated by cell-matrix and cell-cell contacts. Some of those mechanical signals can further regulate downstream signaling pathways associated with cell death processes, wound healing and the like. Cancer cells and normal cells respond to mechanical stimuli differently. Cancer is a disease where the cells exhibit altered biomechanical properties. Early studies determined that cancer cells grew on soft agar whereas normal cells did not. More recent studies show that more than seventy-five percent of 40 randomly selected cancer lines lack the ability to sense rigidity of surrounding matrices.

It is observed that apoptosis of cancer cells can be triggered by periodic stretching of the cancer cells. Unlike conventional ultrasound ablation which causes cell death due to heat or high temperature, rupture, or ejection, cancer cells and/or metastasized cells treated by the provided methods and systems become apoptotic under low intensity, long periods of mechanical stimuli thereby reducing the damage to normal cells caused by either thermal effects and/or cavitational effects. The provided immersion mechanotherapy may utilize periodic forces generated in a combination of duration, magnitude, and frequency that are sufficient to distort the internal organelles to trigger mechanically-induced apoptosis, while the generated periodic forces are small enough such that the normal cells and healthy tissues are not damaged.

Additionally, conventional ultrasound ablation may not be an option for treating metastasized cells due to the wide spread of the tissues and regions to be treated and such ablation may cause high risk and unnecessary damage to a patient. Furthermore, the conventional high intensity ultrasound ablation may not be properly focused in many deeper regions and cannot be safely transmitted through healthy tissue. In contrast, due to the highly-selective and direction-insensitive nature of the present immersion mechanotherapy, methods and systems of the present disclosure may effectively kill metastasized cells or treat metastatic diseases with little negative side effects. In particular, the low power planar pressure waves utilized by the immersion mechanotherapy can effectively reach deep regions within the patient's body.

In some embodiments, the immersion mechanotherapy of the present disclosure may be provided in the form of therapeutic spas and/or hot tubs for ultrasonic treatments, facilitated with configurable and controllable ultrasound generators (e.g., phased arrays or sliding panels of ultrasonic generators). The immersion mechanotherapy may evoke periodic mechanical forces with pre-determined frequency and magnitude to cause tumor cell apoptosis/necrosis without damaging normal tissues (either thermal damage or mechanical damage) as well as to stimulate cells in regenerative processes.

The ultrasound generator-equipped bath tub may be customized and/or personalized according to various treatments or therapies and to accommodate different users. For example, the bath tub may comprise an upwardly open structure adapted to contain a selected volume of liquid which may facilitate ultrasonic waves to the users sitting inside. In another example, the interior wall (e.g., geometry, dimension, material) of the bath tub may be designed to enhance the efficacy of the mechanotherapy. The provided immersion mechanotherapy may be operated at a low ultrasonic frequency and low intensity meanwhile effectively causing cancer/metastasized cell death. The provided immersion mechanotherapy may allow for improved efficacy for cancer treatment (e.g., cancer in any stage) with safety of operation and uniformity of treatment. In particular, the immersion mechanotherapy may comprise offering a home-use embodiment as well as a disposable embodiment that is safe both from the potential shock-hazards but also from the potential over-treatment hazards owning to the force-induced cancer cell death.

In an aspect of the present disclosure, a method is provided for treating metastatic disease using immersion mechanotherapy. The method comprises providing a vessel containing an amount of medium for immersing at least a portion of a subject, and applying one or more programmed cycles of ultrasound waves to the subject through the medium for a pre-determined period of time. Also provided is a device for implementing the immersion mechanotherapy.

In an aspect of the present disclosure, a device is provided for treating target cells in a subject. The device comprises: an immersion element containing a liquid medium to immerse a body part of the subject, and one or more ultrasound transducers configured to generate a sequence of programmed cycles of waves to the body part through the liquid medium thereby applying periodic forces to the target cells for a period of time, and the periodic force applied to the target cells triggers a mechanically-induced apoptotic process in the target cells.

In some embodiments, the target cells comprise cancer cells or metastasized cells. In some embodiments, the immersion element comprises a shape or geometric configuration to regulate a wave field of the sequence of programmed cycles of waves. In some embodiments, the liquid medium is water.

In some embodiments, the one or more ultrasound transducers are mounted to a robotic arm. In some cases, the robotic arm is controlled to position the one or more ultrasound transducers into a desired location or orientation. In some embodiments, the one or more ultrasound transducers are phased array ultrasound transducers. In some embodiments, the one or more ultrasound transducers are sealed and water-proof.

In some embodiments, a frequency of the periodic force is in a range of 30 kHz to 250 kHz. In some embodiments, a frequency of the periodic force is in a range of 5 kHz to 50 kHz. In some embodiments, a frequency of the periodic force is in a range of 150 kHz to 1 MHz.

In some embodiments, the periodic force promotes or preserves survival and growth of normal cells of the subject. In some embodiments, a frequency, magnitude of the periodic force and the period of time are determined based at least in part on the type of the target cells. In some embodiments, the sequence of programmed cycles of waves are generated according to a treatment plan or a type of therapeutic procedure. In some cases, the treatment plan is generated using machine learning techniques. In some embodiments, the device further comprises a controller configured to control the one or more ultrasound transducers based on sensor data.

In a related yet separate aspect, a method is provided for treating target cells in a subject. The method comprises: providing an immersion element containing a liquid medium for immersing a body part of the subject; and generating, by one or more ultrasound transducers, a sequence of programmed cycles of waves to the body part through the liquid medium thereby applying periodic forces to the target cells for a period of time, and the periodic force applied to the target cells triggers mechanically-induced apoptotic process in the target cells.

In some embodiments, the target cells comprise cancer cells or metastasized cells. In some embodiments, the immersion element comprises a shape or geometric configuration to regulate a wave field of the sequence of programmed cycles of waves. In some embodiments, the liquid medium is water.

In some embodiments, the one or more ultrasound transducers are mounted to a robotic arm. In some cases, the robotic arm is controlled to position the one or more ultrasound transducers into a desired location or orientation. In some embodiments, the one or more ultrasound transducers are phased array ultrasound transducers. In some embodiments, the one or more ultrasound transducers are sealed and water-proof.

In some embodiments, a frequency of the periodic force is in a range of 30 kHz to 250 kHz. In some embodiments, a frequency of the periodic force is in a range of 5 kHz to 50 kHz. In some embodiments, a frequency of the periodic force is in a range of 150 kHz to 1 MHz.

In some embodiments, the periodic force promotes or preserves survival and growth of normal cells of the subject. In some embodiments, a frequency, magnitude of the periodic force and the period of time are determined based at least in part on the type of the target cells. In some embodiments, the sequence of programmed cycles of waves are generated according to a treatment plan or a type of therapeutic procedure. In some cases, the method further comprises generating the treatment plan using a machine learning algorithm trained model. In some embodiments, the method further comprises controlling the one or more ultrasound transducers based on sensor data.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein) of which:

DETAILED DESCRIPTION

Figure 1:
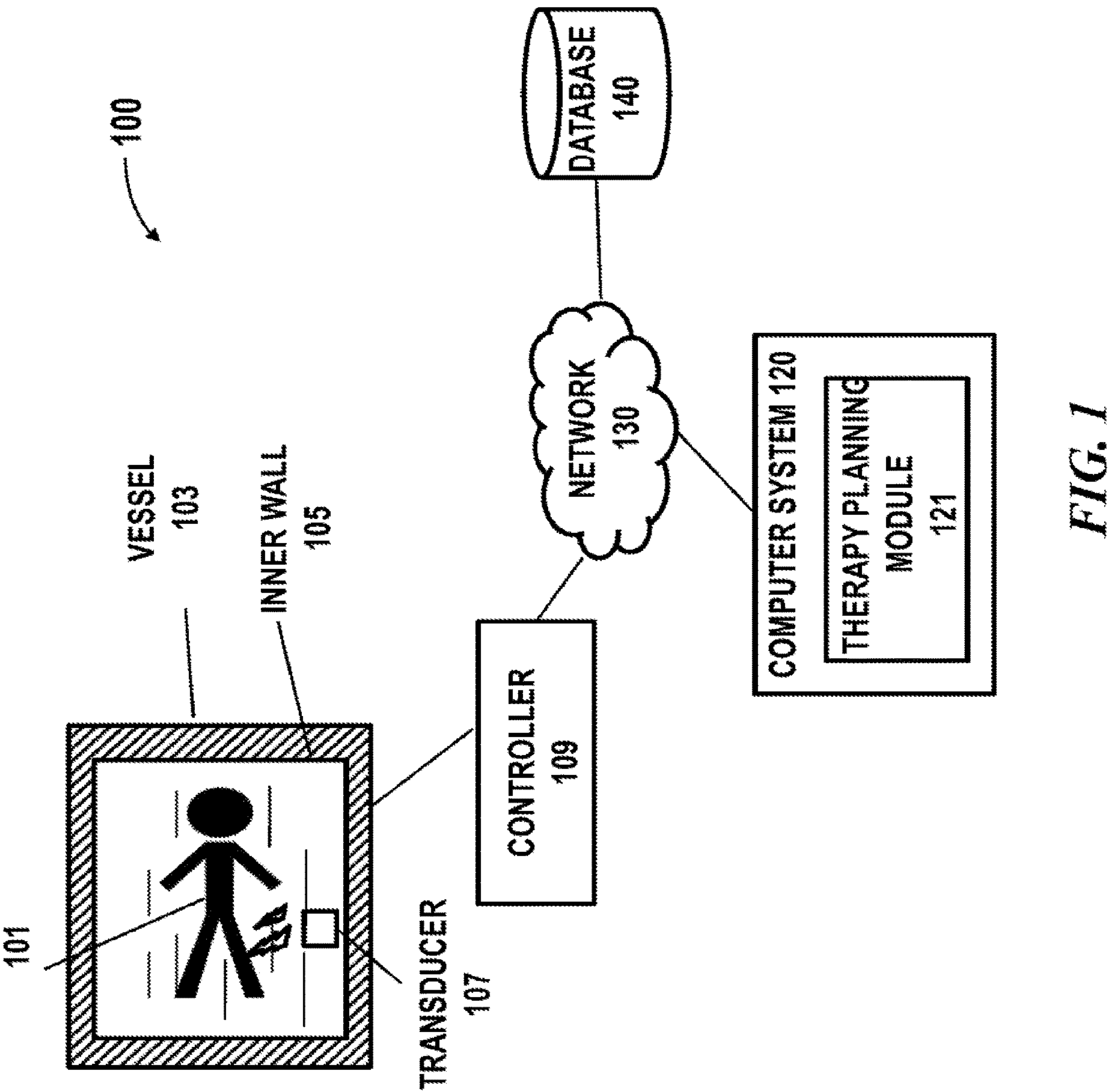
FIG. 1 schematically shows an example system in which immersion mechanotherapy can be conducted, in accordance with some embodiments of the invention.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used herein and in the appended claims, the singular forms "a," "and," and "the" include plural referents unless the context clearly dictates otherwise. Thus, for example, reference to "a programmed cycle" includes a plurality of programmed cycles, reference to "a wave" includes a plurality of waves, and reference to "the signaling pathway" includes reference to one or more signaling pathways (or to a plurality of signaling pathways) and equivalents thereof known to those skilled in the art, and so forth.

The term "about" when referring to a number or a numerical range means that the number or numerical range referred to is an approximation within experimental variability (or within statistical experimental error), and thus the number or numerical range may vary between 1% and 15% of the stated number or numerical range.

When a range of values is provided for describing properties, such as frequencies, or penetration distances, it is understood that each intervening value, to the tenth of the unit of the lower limit unless the context clearly dictates otherwise, between the upper and lower limit of that range, and any other stated or intervening value in that stated range, is encompassed within the disclosure provided herein. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure provided herein.

The term "and/or" as used herein is a functional word to indicate that two words or expressions are to be taken together or individually. For example, A and/or B encompasses A alone, B alone, and A and B together.

The term "comprising" (and related terms such as "comprise" or "comprises" or "having" or "including") is not intended to exclude that in other embodiments, for example, an embodiment of any composition of matter, composition, method, or process, or the like, described herein, may "consist of" or "consist essentially of" the described features.

The term "treating" refers to inhibiting, preventing, curing, reversing, attenuating, alleviating, minimizing, suppressing or halting the deleterious effects of a disease and/or causing the reduction, remission, or regression of a disease. Those of skill in the art will understand that various methodologies and assays can be used to assess the development of a disease, and similarly, various methodologies and assays may be used to assess the reduction, remission or regression of the disease.

Mechanotherapy

In an aspect of the present disclosure, an immersion mechanotherapy is provided for generating and imparting periodic forces to cancer cells and/or metastasized cells in a subject in need thereof. The immersion mechanotherapy may comprise applying one or more programmed cycles of waves to the subject in a uniform and immersion liquid for a pre-determined period of time. The programmed cycles of waves impart periodic forces with controlled duration, magnitude, and frequency that are sufficient to distort the target cells (e.g., cancer cells and/or metastasized cells) such that a mechanically-induced apoptotic process is triggered. The generated periodic forces may have low intensity and be small enough such that the normal cells and healthy tissues that the periodic forces act on may not be subjected to mechanical or thermal damage.

In some cases, the frequency and magnitude of the periodic forces may be pre-determined based on the target disease. A sequence of programmed cycles of waves may be applied to the subject (e.g., patient whole body, a body part, a portion of the patient body) at a frequency in a range of about 20-250 kHz, with low intensity for a long period of time (e.g., hours) so as to produce apoptosis often involving calcium mediated-calpain activation in the target cells (e.g., cancer cells and/or metastasized cells) meanwhile promoting or preserving vitality and healing in normal cells of the subject being treated. The programmed cycles of waves can be in any range below 20 kHz or above 250 kHz so long as the periodic forces imparted on the subject (e.g., internal organelles) mechanically distort the target/normal cells such that a mechanically-induced apoptotic process is triggered in the target cells. In some cases, the frequency, magnitude of the periodic forces, or the period of time of a treatment session may be determined based on the target disease and/or the body part/portion to be treated (e.g., whole body, arm, leg, breast, etc.).

The term "spontaneous cell death" as used herein includes but is not limited to apoptosis, autophagy, and certain forms of necrosis. In the present disclosure, the spontaneous cell death may be caused by a periodic and repetitive sequence of forces which is different from cell death caused by increased amplitude or intensity as in the conventional ablation treatment.

The term "apoptosis" as used herein refers to a regulated network of biochemical events which eventually lead to cell suicide, and is characterized by readily observable morphological and biochemical phenomena, such as fragmentation of the deoxyribonucleic acid (DNA), condensation of the chromatin, chromosome migration in cell nuclei, the formation of apoptotic bodies, mitochondrial swelling, and the like. Inhibition or dysregulation in apoptotic cell death machinery is a hallmark of cancer cells, which is responsible for both tumor development and progression. The provided methods and systems are capable of activating apoptosis mechanisms in the transformed cells.

The terms "subject," "individual," "user" and "patient" are used interchangeably herein to refer to a vertebrate, preferably a mammal such as a human. Mammals include, but are not limited to, murines, simians, humans, farm animals, sport animals, and pets. Tissues, cells and their progeny of a biological entity obtained in vivo or cultured in vitro are also encompassed. In some cases, the subject may suffer from metastatic cancer or metastatic diseases. Metastasis is the spread of cancer cells to new areas of a patient's body, often by way of the lymph system or bloodstream.

The target cell used in the method of the present disclosure can be any cells that are dysregulated in cell signaling processes such as cell death signaling or wound healing. In some embodiments, the target cell is a cancer cell or transformed cell. The target cells may include metastasized cells or metastatic tumor cells that have spread from the primary site of origin, or where it started, into different areas of the body of a patient. The cancer cell that can be used in the method of the present disclosure includes but is not limited to prostate cancer cells, breast cancer cells, colon cancer cells, lung cancer cells, head & neck cancer cells, brain cancer cells, bladder cancer cells, lymphocytes, ovarian cancer cells, renal & testis cancer cells, melanoma cancer cells, liver cancer cells, cervical cancer cells, pancreatic cancer cells or gastrointestinal cancer cells. In some cases, the target cell may be cells in a diseased tissue that desires regeneration, growth, repair and the like.

In some embodiments, the mechanotherapy may induce or regulate apoptosis of the target cell by exposing the target cells to periodic stretch/pressure forces with pre-determined characteristics. The mechanotherapy may be based on the observation that mechanically-induced stress activates calcium channels to overload cancer cells with $Ca^{2+}$ ions and trigger cell death via apoptosis. In some embodiments, the method of the present disclosure at least partially stimulates, increases, opens, activates, facilitates, enhances activation, sensitizes, or upregulates apoptosis signaling pathways of the target cells. The mechanotherapy may effectively activate the cell surface receptors involved in apoptosis signaling pathways of the target cell. The cell surface receptors may be capable of sensing mechanical cues, radiation or waves. The provided immersion mechanotherapy may apply cyclic and/or structured remote force such as ultrasound waves to the target tissue which effectively alters activities in cancerous and/or metastasized cells that results in apoptosis.

The immersion mechanotherapy of the present invention does not induce a spontaneous cell death in normal cells. The "normal cell" as used herein refers to the basic healthy cell or non-transformed cell with normal functions to maintain correct functioning of tissues, organs, and organ systems. Normal cells may undergo spontaneous cell death as part of normal development, to maintain tissue homeostasis, and in response to unrepairable damage. The one or more cycles of waves may be applied to the normal cells without inducing spontaneous cell death of the normal cells in the tissue of the subject.

In some cases, the subject may be diagnosed with cancer. In particular, the cancer includes but is not limited to prostate cancer, breast cancer, colon cancer, lung cancer, head & neck cancer, brain cancer, bladder cancer, lymphoma, ovarian cancer, renal & testis cancer, melanoma, liver cancer, cervical cancer, pancreatic cancer or gastrointestinal cancer. In some cases, the subject may be subjected to late stage cancer, metastatic cancer or metastatic diseases. Metastasis is the spread of cancer cells to new areas of a patient's body, often by way of the lymph system or bloodstream. In some cases, the subject may desire tissue regeneration on surfaces of wounds caused by surgery, injury or disease. Due to the simultaneous positive effect on the normal cells and negative effects on cancer cells, the provided systems and methods may be capable of providing different types of therapeutic procedures (e.g., cancer treatment, wound healing, tissue repair, tissue regeneration, etc.). For instance, the same device or treatment session may treat cancer and wound healing/tissue regeneration simultaneously. Alternatively, the same device may treat cancer and wound healing/tissue regeneration separately or in different treatment sessions. This may beneficially allow for a uniform platform for use by non-professionals (e.g., home-use) with various functionalities or therapeutic procedures.

The mechanically-induced stress to activate calcium channels may be applied in the form of cyclic waves or cyclic forces. The cyclic forces may be delivered to the target tissue in the form of ultrasound waves or pulses in a spa or hot tub setting. The "wave" as used herein refers to any wave with pre-determined characteristics such as frequencies, energy, intensity, or duty cycle that upon application to a target tissue or target region may deform the cells periodically thereby inducing spontaneous cell death of a target cell. The aforementioned characteristics may be determined such that force may be transduced to the target region to induce periodic membrane stress rather than molecular heating or a static deformation thereby avoiding physical damage to the cells. In some cases, the force-inducing wave or pulses may be administered to the target region by penetrating the skin, bone, muscle, and underlying fascia without inducing damage to any portion of human body other than killing the target cells within the target region. In some cases, the force inducing wave may be transmitted in the form of an unfocussed ultrasound wave. Alternatively or in addition to, the force inducing wave may be transmitted in the form of a focused ultrasound wave to focus on the target region/tissue with reduced impact to the untargeted region/tissue.

The various characteristics of the cyclic force such as intensities, frequencies, amplitude and the like may refer to the intensity, frequency or amplitude levels at the effective tissue site or the force imparted on the target cells. As an example, the force may comprise low intensity cycles applied to the tissue site over hours. In some cases, the cyclic force delivered directly to the tissue site or target cells may be occur over long irradiation times (e.g., hours) at low-frequency (e.g., 5-30 kHz, 30-250 kHz, 150 kHz to 1 MHz, etc.) and at low intensity levels (e.g., <500 mW/cm$^2$). The cyclic force may also be referred to as wave, waveform, structured force, structured waveform and the like which are used interchangeably throughout the specification unless context suggests otherwise. The cyclic force may be transmitted to the subject while the subject is immersed in liquid contained in a hot tub.

The waveform may be in any suitable forms/pattern to achieve a uniform membrane stress on the target cell/normal cell. In some cases, the waveform may approximate a sine wave. When such force is applied to the target cell/normal cell, the cell shape changes from a lateral ellipsoid shape to a longitudinal shape then springs back in a cyclic manner while the stress on the membrane may remain relatively constant. In some cases, the waveforms may be determined based on the type of target cells or diseases. For instance, the waveforms delivered to the target tissue may be different according to the different types of cells (e.g., breast cancer cells, fibrosarcoma cells, ovarian carcinoma cells, etc.). In some cases, the waveforms delivered to the target tissue may be dependent on the mechanical properties of the target cell (e.g., dynamic and kinematics properties, inertia of a cell, resonant frequency, etc.).

The waveform applied to the subject may not be direction-sensitive. The waveform in an optimal frequency range with pre-determined amplitudes may expose target cells/normal cells to cyclic deformations due to acceleration without exerting constant pressure. For example, when the force is applied to the cells at a relatively low frequency (e.g., 20-250 kHz), the cell shape may change from a lateral ellipsoid shape to a longitudinal shape then spring back in a cyclic manner while the stress on the membrane may remain relatively constant. Such kind of cyclic force may also be referred to as diffuse forces as they do not have specific direction. This may beneficially allow for an immersed and uniformity therapy that does not require accurate alignment or orientation of the ultrasound device with respect to the subject. For example, for any portion of the subject immersed in the liquid of the hot tub, the administered ultrasound waves may not induce side effects on the normal cells while the efficacy of the treatment may be substantially the same. In some cases, the waveform and intensity may be determined based on empirical data or automatically adjusted according to local measurements and/or live feedback. For instance, the waveform and/or intensity may be automatically adjusted based on measured patient physiological metrics or other real-time conditions.

In some cases, the waveform transmitted to and experienced at the site of the target tissue or target cells may be in a low intensity range. For example, low intensity may be no more than 450 mW/cm$^2$, 400 mW/cm$^2$, 350 mW/cm$^2$, 300 mW/cm$^2$, 250 mW/cm$^2$, 200 mW/cm$^2$, 150 mW/cm$^2$, 100 mW/cm$^2$, 50 mW/cm$^2$, mW/cm$^2$, 10 mW/cm$^2$, or any number below 450 mW/cm$^2$ or above 10 mW/cm$^2$.

In some cases, the waveform experienced at the site of the target tissue or target cell may have frequency in an optimal range based on the mechanical properties of the target cell. For example, the frequency may be in the range from about 5 kHz to 30 kHz, 30 kHz to about 100 kHz, 30 kHz to about 150 kHz, 30 kHz to about 200 kHz, 30 kHz to about 250 kHz, 40 kHz to about 100 kHz, 40 kHz to about 150 kHz, 40 kHz to about 200 kHz, 40 kHz to about 250 kHz, 50 kHz to about 100 kHz, 50 kHz to about 150 kHz, 50 kHz to about 200 kHz, 50 kHz to about 250 kHz, 60 kHz to about 100 kHz, 60 kHz to about 150 kHz, 60 kHz to about 200 kHz, 60 kHz to about 250 kHz, 70 kHz to about 100 kHz, 70 kHz to about 150 kHz, 70 kHz to about 200 kHz, 70 kHz to about 250 kHz, 30 kHz to about 210 kHz, 30 kHz to about 220 kHz, 30 kHz to about 230 kHz, 30 kHz to about 240 kHz, 40 kHz to about 210 kHz, 40 kHz to about 220 kHz, 40 kHz to about 230 kHz, 40 kHz to about 240 kHz, 50 kHz to about 210 kHz, 50 kHz to about 220 kHz, 50 kHz to about 230 kHz or 50 kHz to about 240 kHz, 150 kHz to 1 MHz, and levels of ultrasound frequency within these stated amounts.

In some embodiments of the present disclosure, the low intensity force may be delivered by modulating the duty cycle and/or amplitude of the force. In some cases, the amplitude of the force may be sufficient to induce cell shape deformation by certain amount without introducing mechanical damage to the target cells or normal cells. For example, the target cell shape may be deformed by from about 1% to about 5%, from about 3% to about 8%, from about 5% to about 10% under such cyclic force. Given different sizes of the cells in the target tissue, the deformation may range from 0.1 micron to 12 microns. The duty cycle may be selected such that the deformation is cycled rather than static. For instance, within each cycle, the on-off ratio of force pulses may be about 5%, 10%, 15%, 20%, 25%, 30%, 35%, 40%, 45%, 50% 55%, 60%, 65%, 70%, 75%, 80%, 85%, 90%, 95%, and the like. Duty factor may be defined as a percent of time that the signal/force is "on" (e.g., transmitted) within a cycle. The intensity or the amplitude of the periodic waveform/force may be determined such that no thermal damage is introduced in the target tissue or to the subject.

The cyclic force or waveform may be applied to the target tissue or cells over a period of time. The period of time may be in the range of hours. For example, in an immersion therapy, waveforms may be delivered to the subject as a treatment session for about 10 minutes, 20 minutes, 30 minutes, 40 minutes, 50 minutes, 1 hour, 2 hours, 3 hours, 4 hours, 5 hours, 6 hours, 7 hours, 8 hours, 9 hours, 10 hours, 15 hours, 20 hours, 24 hours, 48 hours or more. A treatment session may refer to exposure to the radiation continuously or intermittently. A treatment session may include one or more sub-sessions that may or may not utilize the same cyclic force or waveform. In some cases, the treatment may be repeated for the same or a different length of time, one or more times for days, weeks, months, years, or for the life of the subject. The treatment may be continuously conducted while the subject is sitting in the hot tub. Alternatively or in addition to, the treatment may be repeated with pre-determined time intervals in between.

As used herein, the plurality of characteristics of the waves or cyclic force such as intensities, amplitude and frequencies are the intensity, amplitude and frequency levels at the effective tissue site, not the actual output value of the ultrasound transducer. In some cases, one or more characteristics of the wave as direct output from the ultrasound transducer may be different from those of the cyclic force effective at the target tissue or target region. For example, the waveform transmitted to and experienced at the site of the target tissue or target cells may be a cyclic force at a low-frequency (e.g., 20-250 kHz) and low intensity level (e.g., <500 mW/cm$^2$).

The output of the ultrasound transducer that generates such waveforms may have a greater intensity level than the resulting effective amount at the target tissue site because of energy loss during transmission. For example, a certain amount of energy may be absorbed by the biologic tissue (e.g., skin, bone, muscle, and underlying fascia) and the liquid in the bath tub while the ultrasound pulses penetrate such biologic tissue and liquid until they reach the target tissue/region. Owing to the low frequency characteristics of the cyclic force, the energy loss may be low and the penetration depth may be long. As an example, no more than 5%, 10%, 15%, 20%, 25%, 30%, 35%, 40%, 45%, 50%, 55%, 60%, 65% of energy may be absorbed when transmitting the waves, and the penetration may reach a depth of at least about 0.1, 0.5, 1, 2, 3, 4, 5, 6, 7, 9, 10, 15, 20, 30, 40, 50 cm or more into a human body. This may advantageously allow for an immersion mechanotherapy that the mechanical waves can be effectively transmitted to an internal tissue of an individual through a pool/container of liquid. Moreover, owing to the low frequency and low intensity characteristics of the cyclic force, heat generated as a result of the waves penetrating the tissues may be greatly reduced.

The cyclic forces may be applied to the subject in the form of an immersion mechanotherapy. In some embodiments, at least a portion of the body of the subject is immersed in a liquid contained in a tub/vessel. Such portion of the body of the subject can be, for example, 0.5%-100% of the body of the subject. In particular, the subject can have 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95% or 100% part of the body immersed in the liquid. The disclosed ultrasound waves may penetrate through some or all of the part of the body immersed in the liquid and the body part not immersed without inducing side effects or damage to the normal cells/tissues.

Immersion Mechanotherapy Systems and Devices

In another aspect, the present disclosure provides devices and systems configured for implementing the immersion mechanotherapy described above in a subject in need thereof. The devices or systems may comprise a vessel or container for containing a liquid in which at least a portion of an individual/ subject is immersed, and one or more ultrasound transducers capable of producing one or more programmed cycles of waves for a pre-determined period of time to treat a disease of the individual. The vessel or container may be sized and shaped to hold one or more individuals. In some cases, the vessel or container may comprise an interior shape or geometries to facilitate transmitting the programmed cycles of waves to the individual.

FIG. 1 schematically shows an example system 100 in which immersion mechanotherapy can be conducted, in accordance with some embodiments of the invention. The system 100 may comprise a vessel or container 103 that at least a portion of an individual 101 is immersed in a liquid contained in the vessel. In some cases, the vessel or container may be a bathtub that one or more individuals can sit in. The vessel or container may be sized and shaped to hold one or more individuals or hold at least a portion of an individual. The vessel or container may comprise an interior shape or geometries 105 to facilitate transmitting the programmed cycles of waves to the individual.

The container or vessel 103 may be coupled to one or more ultrasound transducers 107 capable of producing one or more programmed cycles of waves for a pre-determined period of time to treat a disease of the individual. The disease can be any type of cancer as described elsewhere herein. The disease may be a wound in the individual.

The one or more transducers 107 may be configured to generate structured waves as described elsewhere herein. The structured waves may be ultrasound waves that can be of any shape, and can be focused or unfocused. The ultrasound transducer(s) may be a single element or an area ultrasound transducer, or complex ultrasound generator. In some cases, de-focus techniques such as frequency sweep, jittering, or beam steering may be employed to prevent local peak stress and heating.

Figure 2A:
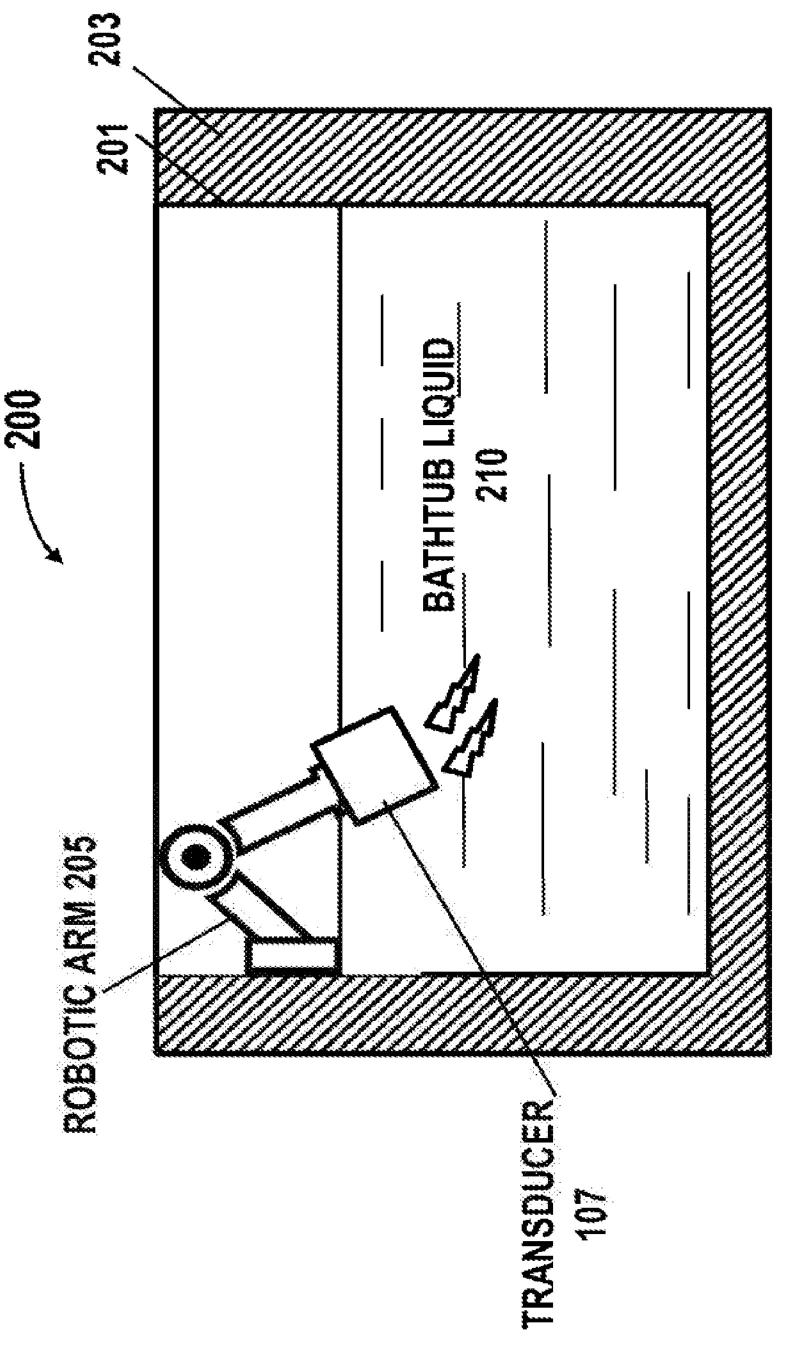
FIG. 2A shows an example of a bathtub coupled with a plurality of ultrasound transducers, in accordance with some embodiments of the present disclosure.
Figure 2A:
Figure 2B:
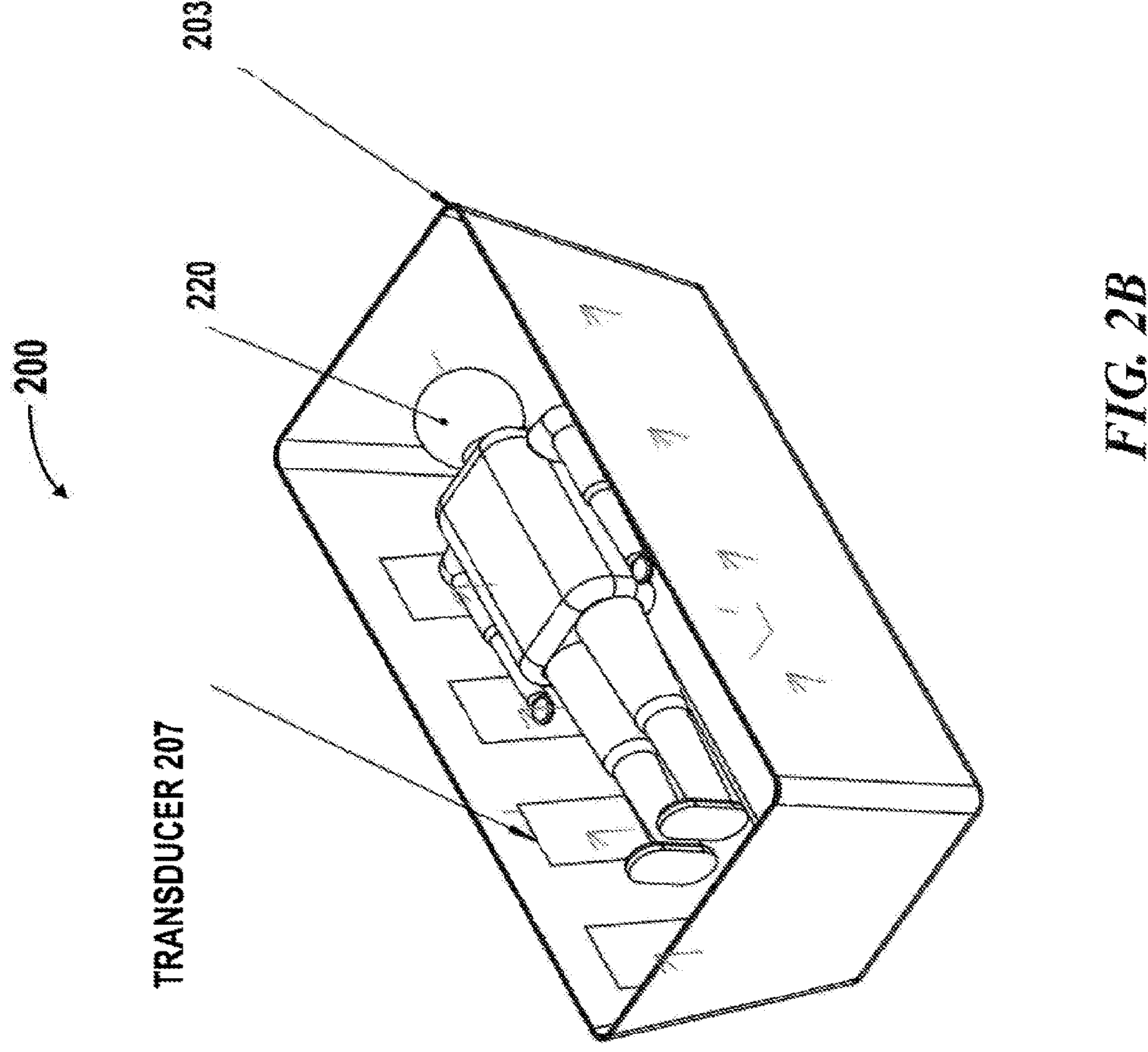
FIG. 2B shows an example of a bathtub coupled with a plurality of ultrasound transducer arrays, in accordance with some embodiments of the present disclosure.

In an example, an array of ultrasound transducers may be utilized in the system 100. The array of ultrasound transducers may be located on one or more sides of the bathtub. FIG. 2A and FIG. 2B show an example of a bathtub 200 coupled to a plurality of ultrasound transducers 107, 207. The plurality of ultrasound transducers 107, 207 may be disposed to a bottom, and side walls 203 of the bathtub. In some cases, the plurality of ultrasound transducers may be mounted at spaced locations on the side wall and/or the bottom. In some embodiments, the one or more transducers may be displaced in the inside space of the vessel such as using a waveguide. In some embodiments, the one or more transducers may be displaced outside the vessel. In some embodiments, the one or more transducers may be positioned close to the bottom wall of the vessel. In some embodiments, the one or more transducers may be positioned close to the side wall of the vessel. In some embodiments, the one or more transducers may be immersed in the liquid 210 in the vessel. The one or more transducers may be arranged at desired locations (e.g., with optimal spacing, orientation with respect to each other) such that when the transducers operate concurrently, ultrasound waves may be generated collectively to achieve a desired effect (e.g., direction, focal plane, intensity, etc.).

In some embodiments, the one or more transducers 107, 207 may be packaged and sealed in a panel for sterilization purpose. The panel may have a substantially smooth surface and may be composed of a material that can be sterilized by normal methods that are compatible with the bathtub, such as steam, heat and pressure, chemicals and the like. In some embodiments, the panel may be disposable. The panel may be removably coupled to the one or more transducers. In some cases, the panel may be composed of materials and may comprise geometries (e.g., thin-walled or sheet) so as to reduce the wave resistance. In some cases, the panel may comprise docking features or structures to mate with a shape of the one or more transducers thereby providing a snug fit.

The one or more ultrasound transducers 107, 207 may or may not be in direct contact with the liquid 210. The one or more ultrasound transducers may or may not be in direct contact with the bathtub. When an individual 220 is positioned into the bathtub, the individual may or may not be in direct contact with the one or more ultrasound transducers.

The one or more ultrasound transducers 107, 207 may be removably coupled to the bathtub or permanently affixed to the bathtub. In some cases, the one or more ultrasound transducers may be attached to the wall 203 of the bathtub. For instance, as shown in FIG. 2B, a transducers array 207 (e.g., phased array ultrasound) may be coupled to the wall of the bathtub and direction of sound waves may be controlled using beamforming techniques. For instance, adjacent transducers may have a constant progressive phase shift or variable phase shift thereby adjusting the beam/wave direction. In some cases, the frequencies of the transducers used may be in a simple design, such that all frequency ranges are the same, or may be in a complex design, in which different transducers have different frequency ranges thereby providing a composite waveform including multiple frequency components or modulation product.

The one or more ultrasound transducers may be sealed and water-proof. The one or more ultrasound transducers or the ultrasound device may be provided with an internal cooling system to stabilize an operation temperature of the one or more transducers. Any suitable cooling methods can be utilized for cooling the ultrasound device. The cooling method can be passive cooling such as by arranging the ultrasound probe to be thermally coupled to a heat sink or other cooling feature (e.g., heat pipe, heat spreader, etc.). Passive cooling may refer to dissipation of heat from an ultrasound transducer (e.g., ultrasound probe) by thermal contact with a heat sink or cooling fins. In some cases, coolant such as fluid coolant or gas coolant may be circulated over the surface of the ultrasound transducers, cooling fins and/or heat sinks to aid in passive cooling. The cooling method can be active cooling such as utilizing a thermoelectric cooler driven by temperature controller to adjust or stabilize the ultrasound transducers operating temperature.

In some embodiments, the one or more transducers 107 may be carried by a robotic arm 205 as shown in FIG. 2A. The robotic arm may be configured to provide one or more degrees of freedom of motion to the one or more transducers. The one or more transducers may be controlled to be positioned at a desired location or orientation so that different portions of the body may be treated. The location or orientation of the one or more transducers may be fixed during a treatment session. Alternatively or in addition to, the one or more transducers may be controlled to move (e.g., sweep motion, positioned to different locations in different sub-sessions) during a treatment session.

In some cases, the robotic arm may be a gantry, such as a three-axis gantry. The robot arm may be a 6-axis robot arm. The robot arm may be capable of motion about 1 or more, two or more, three or more, four or more, five or more, or six or more axes of motion. The robot arm may comprise one or more, two or more, three or more, four or more, five or more, six or more, seven or more, eight or more, nine or more, or ten or more joints. The joints may comprise actuators that may allow various support members to move relative to one another. The robot arm may comprise one or more, two or more, three or more, four or more, five or more, six or more, seven or more, eight or more, nine or more, or ten or more support members. In one example, a first support member may bear weight of an end effector. A second support member may bear weight of the first support member and/or the end effector, and so forth. The actuators may allow rotation of one or more support members relative to one another. One or more sliding mechanisms may be provided that may allow lateral displacement. The robot arm may have a free range of motion that may match or exceed the range of motion of a human arm. Ball and socket joints may or may not be employed by the robot arm.

In some embodiments, the one or more transducers 107 may be affixed to the end effector of the robotic arm 205. Position and orientation of the one or more transducers may be controlled by controlling the robotic arm. In some cases, the robotic arm may be controlled by a robotic controller. The robotic controller may be the controller 109 controlling the one or more transducers or a separate controller. Regarding the control system, cascaded proportional- integral-derivative (PID) may be used to control the attitude and velocity of the robotic arm. It should be noted that there are a variety of control algorithms that can be used to control a gimbal or carrier system, including but not limited to: ON-OFF, PID modes, feedforward, adaptive, intelligent (Fuzzy logic, Neural network, Expert Systems and Genetic) control algorithms. For a specific control model, such as PID control, the control system can be different according to different control objective/output variables (e.g., angular velocity, angular position, angular acceleration, or torque) and different input variables (e.g. input voltage). Accordingly, control parameters may be represented in various ways.

In some cases, the robotic arm controller may be configured to control the robotic arm using sensor data as feedback information. The sensor data may be related to the location of the end effector (i.e., the one or more transducers) with respect to a subject. In some cases, sensors such as proximity sensor or imaging sensor may be used to provide such location/proximity information. In some cases, the one or more ultrasonic transducers along with receivers may be provided as ultrasonic sensor to determine the proximity. In some cases, additional sensors may be included to provide such information.

In some cases, the robotic arm 205 may automatically position the one or more transducers to an initial position. In some embodiments, the robot arm 205 can be passively moved by a user. In such cases, a user may push the arm 205 in any position and the arm 205 compliantly moves. The robotic arm 205 can also be controlled in a compliant mode to improve human robot interaction. For example, the compliant motion control of the robotic arm 205 may employ a collision avoidance strategy and the position-force control may be designed to save unnecessary energy consumption while reducing impact of possible collisions.

The plurality of ultrasound transducers 207 may operate collectively to generate a sequence of force pulses. The number of transducers may be any number such as a number from 1 to 1000, and may have different amplitudes and/or a phase relationship. For instance, adjacent transducers may have a constant progressive phase shift or variable phase shift thereby adjusting the beam/wave direction. In some cases, the frequencies of the transducers may be in a simple design, such that all frequency ranges are the same, or may be in a complex design, in which different transducers have different frequency ranges thereby providing a composite waveform including multiple frequency components.

The ultrasound may be focused, unfocussed or a combination of both. In some cases, additional elements such as acoustic lenses or reflecting mirrors may be utilized to produce focused ultrasound. The focal plane or focal length of the transducer (array) 207 may be adjusted to direct the beam to the location of a target region in the subject. In some examples, the ultrasound device may comprise an array of individually controlled transducers that allows for beam steering and focusing. Beamforming techniques such as phased array beamforming or beam control methods such as using mirrors of moving acoustic prisms or lenses for adjusting focal length of the device may be utilized. The array of transducers 207 may operate collectively to generate a waveform and transmit the waveform to a target location/region. In addition to the focal length of the ultrasound device, one or more characteristics of the wave such as frequency, duty factor, amplitude, intensity and the like may be modulated by controlling the array of ultrasound transducers.

Alternatively or in addition to, the ultrasound may be unfocussed.

Unfocussed ultrasound waves may travel through the bathtub liquid 210 and/or biological tissues immersed therein. The unfocussed ultrasound may be applied to a diffuse large area/portion of the subject. In some embodiments, the one or more transducers may be configurable such that the provided ultrasound system may be capable to switch between focused ultrasound mode and unfocussed mode, or to operate in dual mode.

In some cases, the one or more transducers 107, 207 may be customized to be a neutral generator to provide additional user safety. For example, with use of transducer or antenna arrays that have net feed voltages adding up to zero or near zero, safe human contact may be provided even in the case of a failure of the insulation. The array of antenna elements can be built with alternating coil direction or transducers with inverted piezo crystals thereby allowing for a zero net voltage. Such alternating direction or inverted piezo crystal designs can be applied to one or more pairs of the antenna elements or the entire antenna array.

Figure 3:
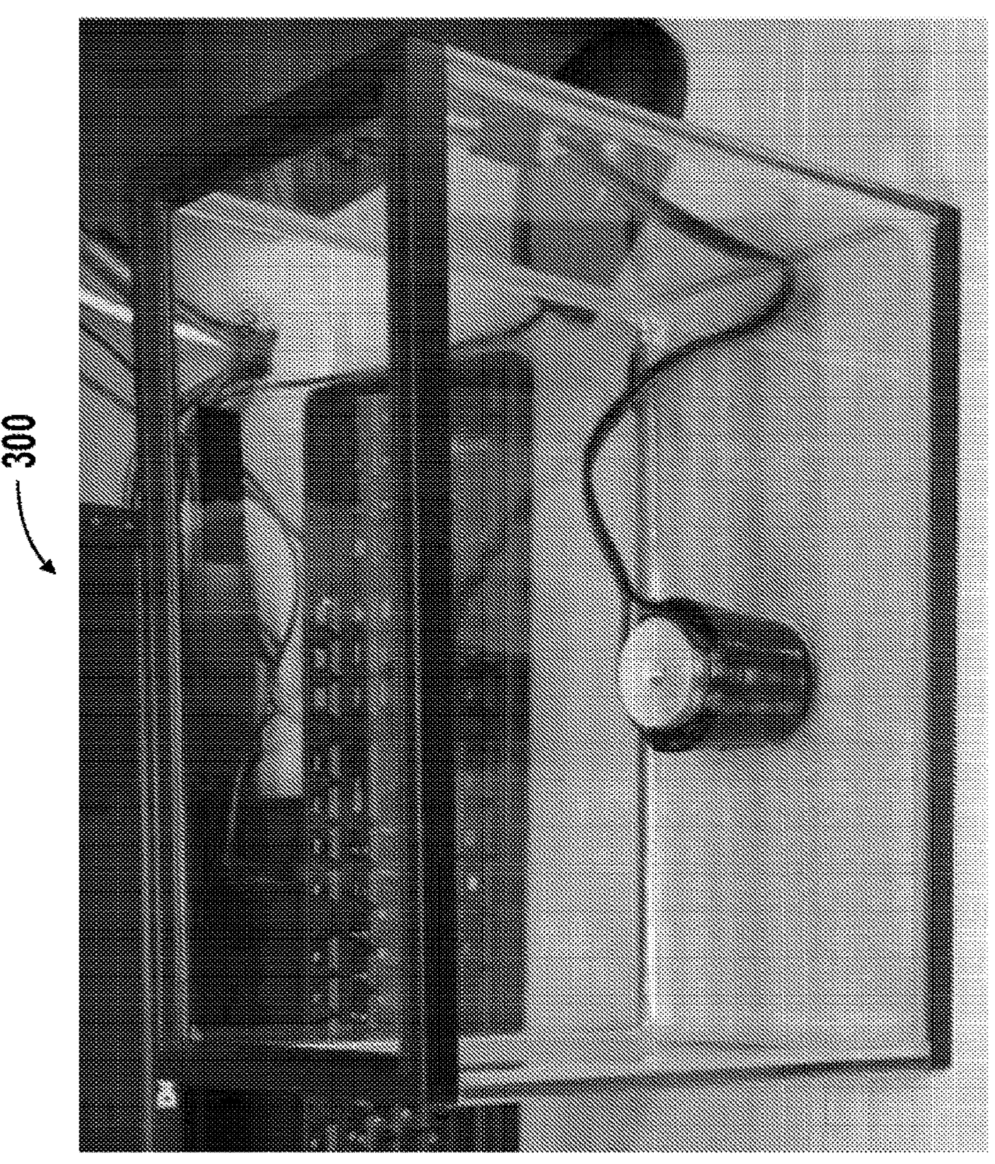
FIG. 3 and FIG. 4 show examples of an ultrasound transducer.
Figure 4:
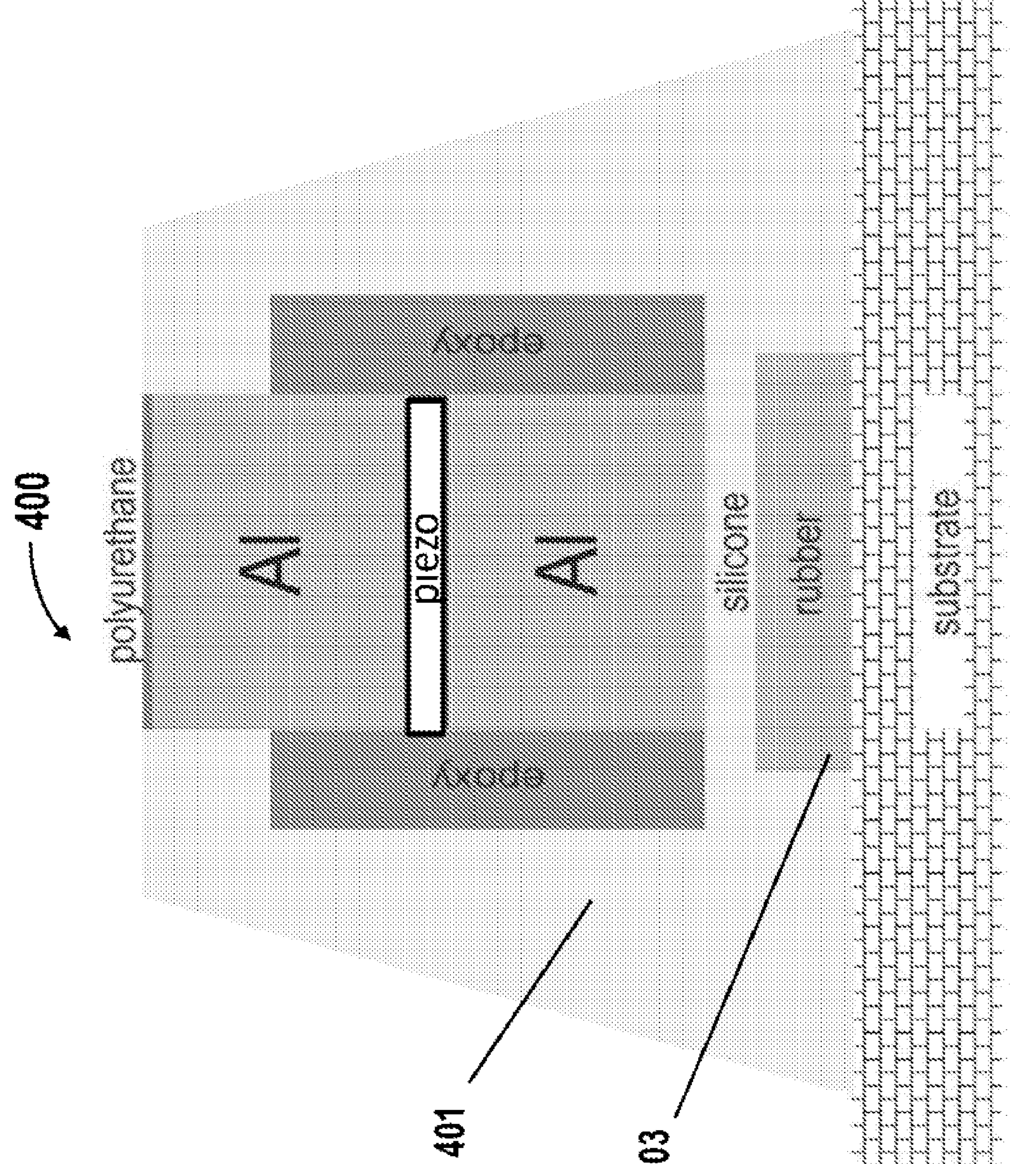

FIG. 3 and FIG. 4 show examples 300, 400 of an ultrasound transducer. In some cases, the ultrasound transducer may comprise a case 401 that is heat conductive and electrically insulated. In some embodiments, the ultrasound transducer may comprise an element such as a rubber 403 displaced at the interface of the case and the substrate for coupling energy to the bathtub/liquid contained therein thereby facilitating transduction of the ultrasonic waves.

Referring back to FIG. 2A and FIG. 2B, the mechanotherapy of the present disclosure can be performed at any appropriate temperature. In some embodiments, the bathtub liquid 210 may be controlled to be at temperature between 4° C. to 45° C., between 16° C. to 20° C., between 20° C. to 40° C., between 36 to 40° C. or any other temperature range based on a user preference.

In some embodiments of the present disclosure, the immersion mechanotherapy is delivered in the form of spa and a heater may be involved to elevate the water temperature to a level typically in the range of about 95-105° F. In some embodiments, the system may comprise a temperature controlling system. The temperature controlling system may comprise one or more temperature sensors and/or temperature controller for controlling the temperature of the medium (e.g., bathtub liquid) as needed. The one or more temperature sensors can be positioned at any suitable location with respect to the bathtub. The temperature can be manually adjusted by an individual, a user, an operator or be automatically controlled according to a pre-programmed therapy plan.

In some embodiments of the present disclosure, the system may also comprise features for cooling an overheated medium or bathtub liquid. For example, or water pumping or recycling may be used to keep the water temperature stable. Such features can be the same as those known in typical spa or massage devices. For instance, the water may be filtered and properly heated, and may be normally recycled to the spa through one or more hydrotherapy massage jet nozzles mounted at spaced locations on the side wall. The bathtub can be equipped with any other massage features such as massage jet nozzles but the presence of bubbles will interfere with the ultrasound transmission and will be avoided.

The medium used in the mechanotherapy of the present disclosure can be any medium that can transduce the ultrasound wave of the present disclosure. In some embodiments, the medium is a liquid. In some embodiments, the medium is a gel. In some embodiments, the medium is water. In some embodiments, the medium is alcohol or saline water.

In some embodiments, the bathtub liquid 210 may be water. The bathtub liquid can be any suitable liquid that is safe to human contact and has an acoustic impedance helpful for coupling ultrasound to the individual. For example, the acoustic impedance may be similar to, or higher than, that of the tissues/skin of the subject to be treated. In some cases, chemicals may be added to the water. The chemicals that can be used in the medium can be any chemicals facilitating the transduction of the wave of the present disclosure. In some cases, the chemical is a salt. In some cases, chemical agents, such as chlorine may be periodically added to the spa water in prescribed amounts suitable for preventing growth of bacterial organisms, to maintain the water in a hygienic state. Other chemical agents such as a sanitizer, may also be periodically added to the water.

In some embodiments, a part of the body of the subject is immersed in the bathtub liquid 210. Said part of the body of the subject can be, for example, 0.5%-100% of the body of the subject. In particular, the subject can have 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95% or 100% part of the body immersed in the liquid.

In some embodiments, the vessel or bathtub 200 may comprise an open-top-end enclosure including a bottom wall and one or more side walls. In some embodiments, the vessel may comprise a bottom wall, opposed sidewalls and opposed end walls. In some embodiments, the vessel may further comprise an openable top lid.

The bottom wall and/or side wall of the vessel 200 can be any appropriate shape. For example, the shapes of the bottom wall or side wall of the vessel may include but are not limited to round, oval, rectangular, square, trapezoidal, triangular or irregular shape. In some embodiments, an interior wall 201 of the vessel may be shaped or have a pre-determined geometric configuration to reflect the ultrasound wave into the immersed part of the subject or a target location. In some cases, the interior wall of the vessel may be shaped to regulate the wave field such that undesired waves (e.g., waves reflected off the interior wall) may be reduced. This beneficially allows for a controlled wave with desired frequency and energy to be received and effective at the immersed body.

Figure 5:
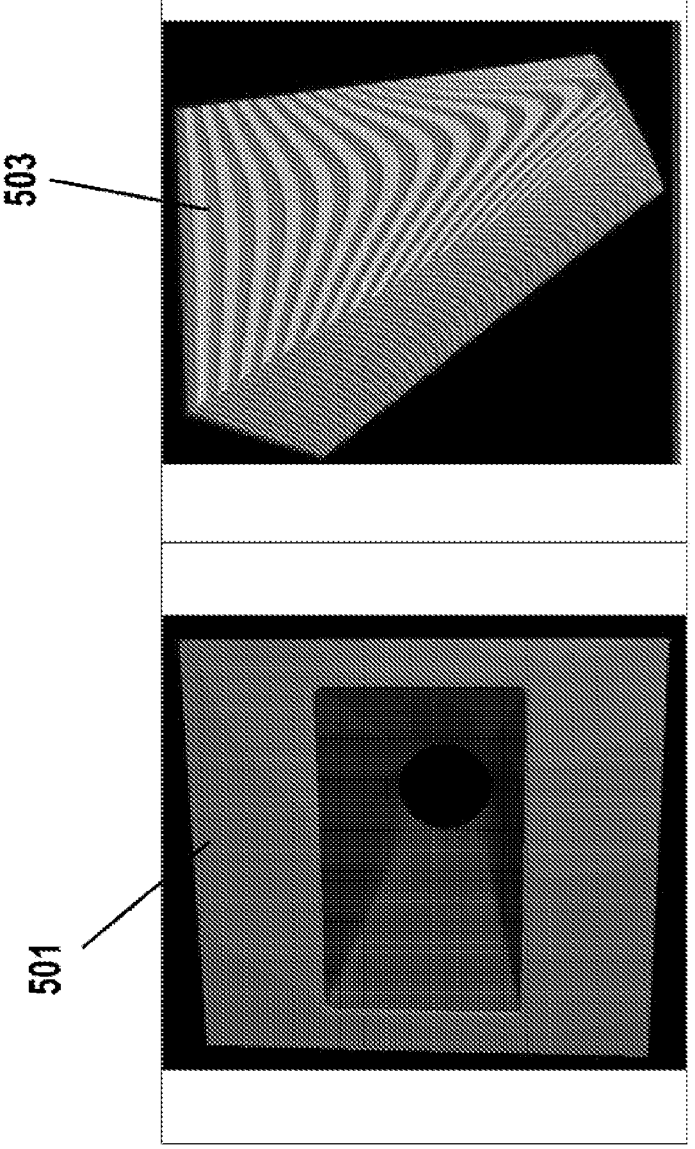
FIG. 5 shows an example of a vessel having an expanding cone-shaped interior wall, in accordance with some embodiments of the present disclosure.

FIG. 5 shows an example of a vessel having an expanding cone-shaped interior wall 501, 503. In some cases, the interior geometries of the vessel may be designed such that a clean far-field wave shape can be achieved. In some cases, in addition to the expanding cone-shaped interior wall, by including a soft medium with scattering kernels therein (e.g., foams or sponges) to the interior surface to absorb ultrasonic waves, undesired sound energy may be dissipated and a regulated sound wave may be transmitted to and received at the immersed body of the subject.

Figure 6:
FIG. 6 shows examples of different waves formed when using a moth eyes-shaped interior surface.
Figure 6:
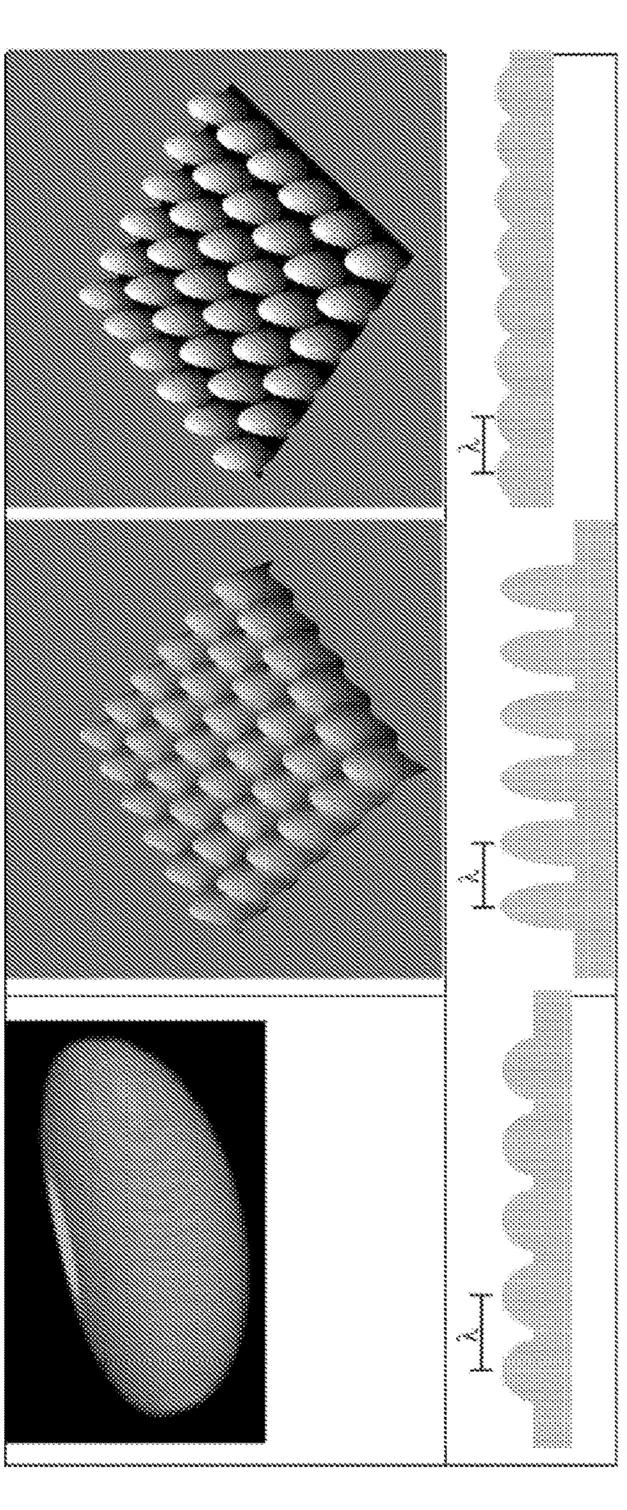

Referring back to FIG. 2A, an interior wall 201 of the vessel may be shaped to reflect the ultrasound wave into the immersed part of the subject or a target location. In some cases, the interior surface 201 of the walls may function as a reflective mirror that may have any suitable profile such as flat, paraboloid surface, Fresnel rings, moth eyes and the like to direct the waves to desired directions. The interior surface may be composed of any suitable material such as glass, aluminum, steel, fiber glass, high temperature ceramics and others. FIG. 6 shows examples of different waves formed when using a moth eyes-shaped interior surface 600. By selecting different focusing and echo surfaces, waves can be focused to a desired direction (e.g., subject) thereby improving energy efficiency.

Referring back to FIG. 2A, the interior surface 210 of the wall may comprise features useful for absorbing excess ultrasonic energy. For example, the interior surface may comprise a soft medium with scattering kernels therein (e.g., foams or sponges) to absorb ultrasonic waves irradiated onto the surface.

The dimension and volume of the bathtub may be designed such that at least a portion of an individual can be held therein. In some embodiments, the length of the bottom wall of the immersion element is between 0.5 m to 3.0 m. In some embodiments, the length of the bottom wall of the immersion element is between 1.0 m to 3.0 m. In some embodiments, the length of the bottom wall of the immersion element is between 1.5 m to 3.0 m. For example, the length of the bottom wall of the immersion element can be about 0.5 m, 0.6 m, 0.7 m, 0.8 m, 0.9 m, 1.0 m, 1.1 m, 1.2 m, 1.3 m, 1.4 m, 1.5 m, 1.6 m, 1.7 m, 1.8 m, 1.9 m, 2.0 m, 2.1 m, 2.2 m, 2.3 m, 2.4 m, 2.5 m, 2.6 m, 2.7 m, 2.8 m, 2.9 m, 3.0 m, 4 m, 5 m, or any value greater than 5 m.

In some embodiments, the width of the bottom is between 0.5 m to 3 m. In some embodiments, the width of the bottom wall of the immersion element is between 1.0 m to 3.0 m. In some embodiments, the width of the bottom wall of the immersion element is between 1.5 m to 3.0 m. For example, the width of the bottom wall of the immersion element can be 0.5 m, 0.6 m, 0.7 m, 0.8 m, 0.9 m, 1.0 m, 1.1 m, 1.2 m, 1.3 m, 1.4 m, 1.5 m, 1.6 m, 1.7 m, 1.8 m, 1.9 m, 2.0 m, 2.1 m, 2.2 m, 2.3 m, 2.4 m, 2.5 m, 2.6 m, 2.7 m, 2.8 m, 2.9 m, 3.0 m, 4 m, 5 m, or any value greater than 5 m.

In some embodiments, the diameter of the bottom wall of the immersion element is between 0.5 m to 3.0 m. In some embodiments, the diameter of the bottom wall of the immersion element is between 1.0 m to 3.0 m. In some embodiments, the diameter of the bottom wall of the immersion element is between 1.5 m to 3.0 m. For example, the diameter of the bottom wall of the immersion element can be 0.5 m, 0.6 m, 0.7 m, 0.8 m, 0.9 m, 1.0 m, 1.1 m, 1.2 m, 1.3 m, 1.4 m, 1.5 m, 1.6 m, 1.7 m, 1.8 m, 1.9 m, 2.0 m, 2.1 m, 2.2 m, 2.3 m, 2.4 m, 2.5 m, 2.6 m, 2.7 m, 2.8 m, 2.9 m, 3.0 m, 4 m, 5 m, or any value greater than 5 m.

In some embodiments, the height of the side wall of the immersion element is between 0.5 m to 3.0 m. In some embodiments, the height of the side wall of the immersion element is between 1.0 m to 3.0 m. In some embodiments, the height of the side wall of the immersion element is between 1.5 m to 3.0 m. For example, the height of the side wall of the immersion element can be 0.5 m, 0.6 m, 0.7 m, 0.8 m, 0.9 m, 1.0 m, 1.1 m, 1.2 m, 1.3 m, 1.4 m, 1.5 m, 1.6 m, 1.7 m, 1.8 m, 1.9 m, 2.0 m, 2.1 m, 2.2 m, 2.3 m, 2.4 m, 2.5 m, 2.6 m, 2.7 m, 2.8 m, 2.9 m or 3.0 m.

In some embodiments, the immersion element can be a vessel such as can be a tub, a bucket, a tank, a container, or a pool. In some embodiments, the immersion element/vessel can be a bathtub. In some embodiments, the immersion element/vessel is a spa tub. In some embodiments, the immersion element/vessel is swimming pool. In some cases, the immersion elements/vessels may be any existing medical or recreational vessels. For example, an existing vessel may be used in conjunction with ultrasound transducers mounted to the robotic arm to provide the immersion therapy. In another example, the ultrasound transducers may be [a] modular with a quick secure/release mechanism such that a user may conveniently set up the ultrasound transducers with a tub in a home-use scenario.

The material of the immersion element or vessel can be any appropriate type of material including but not limited to glass, metal or ceramic, aluminum and steel, fiber glass, plywood, porcelain and the like. In some embodiments, material of the immersion element/vessel may be high temperature ceramic.

Referring back to FIG. 1, the ultrasound transducers of the system are capable of producing one or more programmed cycles of waves for a pre-determined period of time to induce death of target cells. The one or more programmed cycles of waves may be effective in inducing death of cancer cells and/or promoting healing by normal cells in a subject so that the one or more programmed cycles of waves may treat diseases such as cancer and/or facilitate wound healing. In some embodiments, the frequency of the wave is in a range of 20 to 250 kHz.

In some embodiments, the system 100 may further comprise a user positioning system. In some cases, the user positioning system may utilize proximity sensors to detect location of the user. The proximity sensors may be the ultrasound device where the ultrasound transducer may be paired with one or more receivers to measure a distance based on time of flight. Alternatively or in addition to, additional sensors may be used to locate the body of the subject. For instance, additional proximity sensors (e.g., ultrasonic sensors, cameras) may be used to detect the position of the subject with respect to the vessel/transducer or the proximity of the subject to the transducers.

The controller 109 may control the one or more ultrasound transducers 107 coupled to the vessel. The system 100 may further comprise a computer system 120 and one or more databases 140 operably coupled to the controller 109 over the network 130. The computer system 120 may comprise a therapy planning module 121 implementing methods provided herein for generating therapy plans.

The computer system 120 may be used for generating a personalized therapy plan based on personal/user information, device setup, diagnostic information, and the like. Although the illustrated diagram shows the controller and computer system as separate components, the controller and computer system can be integrated into a single component.

For instance, a therapy plan may comprise information about level of mechanotherapy (e.g., frequency, intensity, amplitude, duty cycle of the ultrasound waves), type of therapy (e.g., cancer treatment, wound healing or both), information about the treatment region (e.g., location, volume, tissue type, etc.), operation settings (e.g., temperature control, focused/unfocused beam), treatment duration, user information (e.g., user preferred spa temperature) or others.

A therapy plan may be generated in a fully automated, semi-automated, or manual fashion. In some cases, the therapy plan may be generated automatically upon receiving a diagnostic input or user information. For instance, the frequency, amplitude, intensity of the ultrasound waves to be delivered may be determined automatically based on the diagnostic information (e.g., tissue location, volume, disease type, application purpose) and/or user information. In some cases, the treatment plan may be generated using AI techniques such as machine learning methods. For instance, machine learning models may be trained for generating a therapy plan. In some cases, the input data supplied to the machine learning model may include diagnostic information, device information, personal information or others as described elsewhere herein. In some cases, the output of the machine learning model can be a therapy plan or one or more parameters of the treatment (e.g., characteristic of forces, device setup, spa duration, etc.). The therapy plan may dynamically adapt to real-time conditions based on feedback information. Alternatively or in addition to, the therapy plan may run through the entire course without real-time feedback information.

Treatment parameters may be tailored to the particular cancer therapy that the patient is receiving, as well as specific aspects of the patient that can be impacted by the mechanotherapy. For example, come drug treatments may enable ultrasound to damage normal tissue, and these would need to be accounted for when developing the treatment parameters. The mechanotherapy can be modified for the specific conditions of the patient in consultation with the patient's physician.

In some cases, the machine learning method used for generating the treatment plan may comprise one or more machine learning algorithms. Examples of machine learning algorithms may include a support vector machine (SVM), a naive Bayes classification, a random forest, a deep learning model such as neural network, feedforward neural network, radial basis function network, recurrent neural network, convolutional neural network, deep residual learning network, or other supervised learning algorithm or unsupervised learning algorithm.

The controller 109 may be operated to provide the ultrasound device controller information about a pulse sequence and/or to manage the operations of the entire system, according to installed software programs. In some cases, the controller may also serve as an element for instructing a subject/user to perform tasks, such as, for example, positioning a part of the body to a given location in the vessel 103 by a voice message produced using an automatic voice synthesis technique. The controller may receive commands from an operator which indicate the mechanotherapy to be performed. Alternatively, the system 100 may be for home-use and the user may receive instruction via a user interface (e.g., mobile application) operably coupled to the computer system via the network 130. The controller may comprise various components such as a pulse generator module which is configured to operate the system components to carry out the desired wave or cyclic force sequence, producing data that indicate the timing, strength and shape of the wave or ultrasound pulses to be produced, and the direction of the beam. In some cases, the controller 109 may control pulse generator module and/or a set of gradient amplifiers of the transducers to control the frequency, amplitude and shape of the pulses or waves to be produced during the therapy. In some cases, the controller 109 may control the phase shifting of phased array transducers to adjust the beam direction, focus, and other properties of the ultrasound waves. In some cases, the controller 109 may control a robotic arm carrying the one or more transducers thereby controlling the orientation and location of the one or more transducers with respect to the subject.

In some situations, the controller 109 may also receive real-time patient data from a physiological acquisition controller that receives signals from sensors attached to the patient, such as ECG (electrocardiogram) signals from electrodes or respiratory signals from bellows. The controller 109 may be coupled to various sensors for monitoring the condition of the patient (e.g., wound healing progress), the ultrasound transducers, and the vessel (e.g., liquid filling, liquid temperature, etc.). For instance, a temperature sensor may be coupled to the controller 109 for temperature control during the operation. In some cases, the system 100 may include a user positioning system that may receive commands to instruct the user to move to a desired location for the treatment or to immerse certain body part in the bathtub water.

In some cases, the controller 109 may comprise or be coupled to an operator console (not shown) which can include input devices (e.g., keyboard) and control panel and a display. In the home-use situations, the operator console may be a user interface. For example, the controller may have input/output (I/O) ports connected to an I/O device such as a display, keyboard and printer. In some cases, the operator console may communicate through the network with the computer system 120 that enables an operator to control the therapeutic procedure or modify a therapeutic plan on a screen of display. In some cases, a user may be allowed to view the disease progress such as wound healing progress on the display.

The system 100 may comprise a user interface. The user interface may be configured to receive user input and output information to a user. The user input may be related to control of a therapeutic procedure (e.g., cancer treatment, wound healing, tissue repair, tissue regeneration, etc.), generating/modifying a therapeutic plan (e.g., select body part to be treated), control of the spa settings (e.g., temperature, massage modes, etc.), and the like. The user input may be related to the operation of the vessel (e.g., massage modes, therapy level, water temperature, etc.), operation of the ultrasound waves (e.g., parameters for controlling the waves to be delivered to the target region such as frequencies, amplitude, duration, etc.). The user input may be related to various operations or settings for generating a therapeutic plan. The user interface may be rendered on a screen such as a touch screen and any other user interactive external device such as handheld controller, mouse, joystick, keyboard, trackball, touchpad, button, verbal commands, gesture-recognition, attitude sensor, thermal sensor, touch-capacitive sensors, foot switch, or any other device.

The system 100 may comprise computer systems 120 and database systems 140, which may interact with the controller. The computer system can comprise a laptop computer, a desktop computer, a central server, distributed computing system, etc. The processor may be a hardware processor such as a central processing unit (CPU), a graphic processing unit (GPU), a general-purpose processing unit, which can be a single core or multi core processor, a plurality of processors for parallel processing, in the form of fine-grained spatial architectures such as a field programmable gate array (FPGA), an application-specific integrated circuit (ASIC), digital signal processor (DSP), and/or one or more RISC Machine processors. The processor can be any suitable integrated circuits, such as computing platforms or microprocessors, logic devices and the like. Although the disclosure is described with reference to a processor, other types of integrated circuits and logic devices are also applicable. The processors or machines may not be limited by the data operation capabilities. The processors or machines may perform 512 bit, 256 bit, 128 bit, 64 bit, 32 bit, or 16 bit data operations.

The system 100 may comprise one or more databases. The one or more databases 140 may utilize any suitable database techniques. For instance, structured query language (SQL) or "NoSQL" database may be utilized for storing diagnostic data, such as image data obtained by suitable imaging modalities, training datasets or trained model for generating therapeutic plan, parameters of a therapeutic plan, historical therapeutic plan, user-preferred spa setting, etc. Some of the databases may be implemented using various standard data-structures, such as an array, hash, (linked) list, struct, structured text file (e.g. ., XML), table, JSON, NOSQL and/or the like. Such data-structures may be stored in memory and/or in (structured) files. In another alternative, an object-oriented database may be used. Object databases can include a number of object collections that are grouped and/or linked together by common attributes; they may be related to other object collections by some common attributes. Object-oriented databases perform similarly to relational databases with the exception that objects are not just pieces of data but may have other types of functionality encapsulated within a given object. If the database of the present disclosure is implemented as a data-structure, the use of the database of the present disclosure may be integrated into another component such as the component of the present invention. Also, the database may be implemented as a mix of data structures, objects, and relational structures. Databases may be consolidated and/or distributed in variations through standard data processing techniques. Portions of databases, e.g., tables, may be exported and/or imported and thus decentralized and/or integrated.

The network 130 may establish connections among the components in the system 100 and a connection of the system to external systems. The network 130 may comprise any combination of local area and/or wide area networks using both wireless and/or wired communication systems. For example, the network 130 may include the Internet, as well as mobile telephone networks. In one embodiment, the network 130 uses standard communications technologies and/or protocols. Hence, the network 130 may include links using technologies such as Ethernet, 802.11, worldwide interoperability for microwave access (WiMAX), 2G/3G/4G mobile communications protocols, asynchronous transfer mode (ATM), InfiniBand, PCI Express Advanced Switching, etc. Other networking protocols used on the network 230 can include multiprotocol label switching (MPLS), the transmission control protocol/Internet protocol (TCP/IP), the User Datagram Protocol (UDP), the hypertext transport protocol (HTTP), the simple mail transfer protocol (SMTP), the file transfer protocol (FTP), and the like. The data exchanged over the network can be represented using technologies and/or formats including image data in binary form (e.g., Portable Networks Graphics (PNG)), the hypertext markup language (HTML), the extensible markup language (XML), etc. In addition, all or some of links can be encrypted using conventional encryption technologies such as secure sockets layers (SSL), transport layer security (TLS), Internet Protocol security (IPsec), etc. In another embodiment, the entities on the network can use custom and/or dedicated data communications technologies instead of, or in addition to, the ones described above.

The systems and devices of present disclosure can be applied in any appropriate site. In some embodiments, the device of the present disclosure may be applied at a hospital. In some embodiments, the device of the present disclosure may be applied at the home place of the subject. In some embodiments, the device of the present disclosure may be applied at a leisure site such as spa, sport center, etc.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

That which is claimed is:

1. A device for treating tumor cells in a subject, the device comprising:

an immersion element containing a liquid medium to immerse a body part of the subject, and one or more ultrasound transducers configured to generate a sequence of programmed cycles of waves to the body part through the liquid medium, the sequence of programmed cycles of waves being generated with a modulation pattern, intensity, and frequency sufficient to apply periodic forces to the tumor cells and non-tumor cells for a period of time that trigger a mechanically-induced apoptotic process in the tumor cells without mechanically damaging the tumor cells and the non-tumor cells, wherein the mechanically-induced apoptotic process is triggered by periodic stretching of the tumor cells, rather than by heat or high temperature, and wherein the modulation pattern, intensity, and frequency are configured to cause stretching and relaxation of the tumor cells sufficient to activate the mechanically-induced apoptotic process.

2. The device of claim 1, wherein the tumor cells comprise cancer cells or metastasized cells.

3. The device of claim 1, wherein the immersion element comprises a shape or geometric configuration to regulate a wave field of the sequence of programmed cycles of waves.

4. The device of claim 1, wherein the liquid medium is water.

5. The device of claim 1, wherein the one or more ultrasound transducers are mounted to a robotic arm.

6. The device of claim 5, wherein the robotic arm is controlled to position the one or more ultrasound transducers into a desired location or orientation.

7. The device of claim 1, wherein the one or more ultrasound transducers are phased array ultrasound transducers.

8. The device of claim 1, wherein the one or more ultrasound transducers are sealed and water-proof.

9. The device of claim 1, wherein the frequency of the periodic forces is in a range of 30 kHz to 250 kHz and power transmitted by the periodic forces is no more than 250 $mW/cm^2$.

10. The device of claim 1, wherein the frequency of the periodic forces is in a range of 5 kHz to 50 kHz and power transmitted by the periodic forces is no more than 250 $mW/cm^2$.

11. The device of claim 1, wherein the periodic forces promote or preserve survival and growth of normal cells of the subject.

12. The device of claim 1, wherein the frequency, magnitude of the periodic forces and the period of time are determined based at least in part on a type of the tumor cells.

13. The device of claim 1, wherein the sequence of programmed cycles of waves is generated according to a treatment plan or a type of therapeutic procedure.

14. The device of claim 13, wherein the sequence of programmed cycles of waves is generated according to the treatment plan and the treatment plan is generated using machine learning techniques.

15. The device of claim 1, further comprising a controller configured to control the one or more ultrasound transducers based on sensor data.

16. A method for treating tumor cells in a subject, comprising:

providing an immersion element containing a liquid medium for immersing a body part of the subject; and generating, by one or more ultrasound transducers, a sequence of programmed cycles of waves to the body part through the liquid medium, the sequence of programmed cycles of waves being generated with a modulation pattern, intensity, and frequency sufficient to apply periodic forces to the tumor cells and non-tumor cells for a period of time that trigger a mechanically-induced apoptotic process in the tumor cells without mechanically damaging the tumor cells and the non-tumor cells, wherein the mechanically-induced apoptotic process is triggered by periodic stretching of the tumor cells, rather than by heat or high temperature, and wherein the modulation pattern, intensity, and frequency causes stretching and relaxation of the tumor cells sufficient to activate the mechanically-induced apoptotic process.

17. The method of claim 16, wherein the tumor cells comprise cancer cells or metastasized cells.

18. The method of claim 16, wherein the immersion element comprises a shape or geometric configuration to regulate a wave field of the sequence of programmed cycles of waves.

19. The method of claim 16, wherein the liquid medium is water.

20. The method of claim 16, wherein the one or more ultrasound transducers are mounted to a robotic arm.

21. The method of claim 20, wherein the robotic arm is controlled to position the one or more ultrasound transducers into a desired location or orientation.

22. The method of claim 16, wherein the one or more ultrasound transducers are phased array ultrasound transducers.

23. The method of claim 16, wherein the one or more ultrasound transducers are sealed and water-proof.

24. The method of claim 16, wherein the frequency of the periodic forces is in a range of 30 kHz to 250 kHz.

25. The method of claim 16, wherein the frequency of the periodic forces is in a range of 5 kHz to 50 kHz.

26. The method of claim 16, wherein the periodic forces promote or preserve survival and growth of normal cells of the subject.

27. The method of claim 16, wherein the frequency, magnitude of the periodic forces and the period of time are determined based at least in part on a type of the tumor cells.

28. The method of claim 16, wherein the sequence of programmed cycles of waves is generated according to a treatment plan or a type of therapeutic procedure.

29. The method of claim 28, wherein the sequence of programmed cycles of waves is generated according to the treatment plan, said method further comprising generating the treatment plan using a machine learning algorithm trained model.

30. The method of claim 16, further comprising controlling the one or more ultrasound transducers based on sensor data.

31. The method of claim 16, further comprising providing different types of therapeutic procedures by adjusting the sequence of programmed cycles of waves.

32. The method of claim 24, wherein power transmitted by the periodic forces is no more than 250 $mW/cm^2$.

33. The method of claim 16, wherein power transmitted by the periodic forces is no more than 250 $mW/cm^2$.

34. The device of claim 1, wherein power transmitted by the periodic forces is no more than 250 $mW/cm^2$.

35. The device of claim 1, wherein the period of time extends for about 2 hours or more.

36. The method of claim 16, wherein the period of time extends for about 2 hours or more.

37. The method of claim 24, wherein the period of time extends for about 2 hours or more.

38. A device for treating tumor cells, the device comprising:

an immersion element containing a liquid medium to immerse a plurality of cells comprising the tumor cells and non-tumor cells, and one or more ultrasound transducers configured to generate a sequence of programmed cycles of waves to the plurality of cells through the liquid medium, the sequence of programmed cycles of waves being generated with a modulation pattern, intensity, and frequency sufficient to apply periodic forces to the tumor cells and non-tumor cells for a period of time that trigger a mechanically-induced apoptotic process in the tumor cells without mechanically damaging the tumor cells and the non-tumor cells, wherein the mechanically-induced apoptotic process is triggered by periodic stretching of the tumor cells, rather than by heat or high temperature, and wherein the modulation pattern, intensity, and frequency are configured to cause stretching and relaxation of the tumor cells sufficient to activate the mechanically-induced apoptotic process.

* * * * *